(12) United States Patent
Coe et al.

(10) Patent No.: US 9,889,069 B1
(45) Date of Patent: Feb. 13, 2018

(54) INTERACTIVE MEDICATION MANAGEMENT SYSTEM

(71) Applicant: One World Design & Manufacturing Group LTD

(72) Inventors: Matthew Coe, Annandale, NJ (US); Fred Pether, New Hope, PA (US); Sean Ely, Flemington, NJ (US)

(73) Assignee: One World DMG, Ltd., Warren, NJ (US)

( * ) Notice: Subject to any disclaimer, the term of this patent is extended or adjusted under 35 U.S.C. 154(b) by 0 days.

(21) Appl. No.: 15/359,662

(22) Filed: Nov. 23, 2016

(51) Int. Cl.
*A61J 7/04* (2006.01)
*H04W 4/00* (2018.01)
*H04Q 9/02* (2006.01)
*G06F 3/041* (2006.01)
*A61J 7/00* (2006.01)
*H04W 84/04* (2009.01)

(52) U.S. Cl.
CPC .......... *A61J 7/0427* (2015.05); *A61J 7/0084* (2013.01); *A61J 7/0418* (2015.05); *A61J 7/0454* (2015.05); *G06F 3/041* (2013.01); *H04Q 9/02* (2013.01); *H04W 4/005* (2013.01); *H04W 84/042* (2013.01)

(58) Field of Classification Search
CPC ... A61J 7/0481; A61J 7/0445; G06F 19/3462; G07F 9/026

USPC ......... 700/240, 243, 244, 232; 221/1, 131.1, 221/119
See application file for complete search history.

(56) References Cited

U.S. PATENT DOCUMENTS

| | | | |
|---|---|---|---|
| 8,195,330 B2 | 6/2012 | Coe | |
| 8,670,865 B2 | 3/2014 | Coe | |
| 2006/0071011 A1* | 4/2006 | Varvarelis | A61J 7/0481 221/9 |
| 2008/0203107 A1* | 8/2008 | Conley | A61J 7/0472 221/1 |
| 2009/0071971 A1* | 3/2009 | Johnston | A61J 7/0481 221/1 |
| 2012/0006847 A1* | 1/2012 | Coe | A61J 7/0481 222/52 |
| 2012/0189177 A1* | 7/2012 | Oh | G06K 9/228 382/128 |
| 2012/0259456 A1* | 10/2012 | Saltsov | A61J 7/0076 700/236 |
| 2014/0277702 A1* | 9/2014 | Shaw | G06F 19/3462 700/232 |
| 2014/0339248 A1* | 11/2014 | Reddy | A61J 7/0076 221/1 |
| 2016/0058661 A1 | 3/2016 | Pether | |

* cited by examiner

*Primary Examiner* — Timothy Waggoner
*Assistant Examiner* — Ayodeji Ojofeitimi
(74) *Attorney, Agent, or Firm* — Mitchell J. Mehlman, Esq.

(57) ABSTRACT

Interactive medicine management systems and methods comprising integrated elements using a network processor to provide assistance to individuals in order to organize and monitor patient compliance in the administration of one or more medications are provided.

13 Claims, 8 Drawing Sheets

INTERACTIVE MEDICATION MANAGEMENT SYSTEM

BACKGROUND OF THE INVENTION

The present invention relates to improved patient compliance devices, systems, and methods. The devices and systems are connected via one or more machine to machine (M2M) communication networks that communicate with one or more medicine storage and dispensing devices. Methods for monitoring and increasing patient compliance with regard to timely and accurate dispensing of medicines using machine to machine networks are provided.

Many people take one or more medicine or supplements, such as minerals or vitamins, several times a day to maintain or improve their health. Often, these medications or supplements must be taken at specific times each day. If medications or supplements are not taken at the proper times, individual health may be jeopardized. For example, failure to take a prescribed medication for treatment of heart disease can result in severe health consequences such as a heart attack or stroke. Similarly, patients that seek to take extra doses before the prescribed time interval can be in danger of an overdose. Non-compliance with a prescribed dose regimen includes patients who fail to take a dose at a prescribed time or patients who take one or more extra doses that are not in compliance with the minimum time between dose of the particular prescription or label instructions for ingestion.

Further, non-compliance with a prescribed regimen of one or more medications, particularly in the elderly and the aging population of "baby boomers", can result in billions of dollars of unnecessary health care costs.

Many people who take one or more medication or supplement a day are able to take medications or supplements without assistance. However, many people who take one or more medication or supplement a day require a reminder or the assistance of a care taker. Care takers may be one or more members of the patient's family or other individuals, such as friends, nurses, nurse's aids and the like. It can be difficult for a patient or a care taker to organize a patient's medications or supplements to insure compliance with a predetermined schedule. Further, it can be extremely difficult to monitor compliance with multiple medication schedules. Failure to properly monitor compliance can result in catastrophic health consequences to the patient and high levels of caretaker anxiety, which can also lead to increased health problems for care givers.

U.S. Pat. No. 8,195,330 to Coe et al. discloses interactive medicine organizers comprising integrated software and hardware elements and multifunctional interactive wireless devices, such as smart phones, to provide assistance to individuals who need to organize or monitor the administration of one or more medications.

U.S. Pat. No. 8,670,865 to Coe et al. discloses interactive medicine organizers and methods comprising integrated software and hardware elements and multifunctional interactive wireless devices to provide assistance to individuals who need to organize or monitor the administration of one or more medications. In one embodiment, an apparatus has a dispenser body and a housing. A lockable sliding door is connected to the housing to allow a user access to items stored within the housing. A rotating tray has one or more chambers. A docking station is connected to the housing. A multifunctional interactive wireless device, such as a smart phone, can dock with the docking station, can command the tray to a plurality of positions, and can command the door to slide between a plurality of locked or unlocked positions. The device executes a software application for determining the plurality of positions of the tray, and the door based on a data set input by a user. The commanding can be performed by physical docking of the multifunctional interactive wireless device with the docking station or wirelessly without physical docking of the multifunctional interactive wireless device with the docking station.

U.S. Pub. No. 20160058661, Pether et al., discloses an apparatus for improving patient compliance comprising a housing. The housing has a lid and a lock for locking or unlocking the lid. A sensor can be configured to detect a position of the lid. A wireless transceiver is used for transmitting the position of the lid to a smart device application. A smart device is capable of wirelessly commanding the lock to an open position or a closed position. The smart device runs a smart device application for determining a pre-determined time for reminding a user to unlock the lid based on a medication data set input by the user and for receiving and recording the position of the lid.

The present invention provides novel devices, systems, and methods for improving the ease of user compliance with a programmable schedule for reminding a user to take one or more medications or supplements and monitoring the compliance for early intervention in the case of non-compliance.

SUMMARY OF THE INVENTION

In one aspect of the invention an apparatus has a housing. A door is connected to the housing. The door can be commanded to an open position or a closed position to allow a user to load or to access a medicine stored within the housing. A carousel has at least one compartment. The carousel is mounted in the housing and can be commanded to rotate the at least one compartment to at least one position associated with a location of the medicine. An interactive touchscreen is connected to the housing. The touchscreen can be configured to command the door to an open or a closed position and to command the carousel to the at least one position associated with a location of the medicine. A processor is capable of communicating with a network. The processor can send or receive a telemetry data set to or from said network for monitoring a compliance of a user with a predetermined medicine schedule In one embodiment of this aspect, the processor can be a machine to machine (M2M) cell radio processor.

In some embodiments of this aspect, the network can be a wireless cell radio network.

In certain embodiments, the network can further include a machine to machine (M2M) secure virtual private network connection.

In some embodiments of this aspect, the telemetry data set can include a name of a medicine, a strength of the medicine, and a time for dispensing the medicine.

In certain embodiments, the telemetry data set can include a time the door was opened, a time the door was closed, and a time the carousel was rotated to the at least one position associated with a location of the medicine.

In a particular embodiment of this aspect, the machine to machine (M2M) processor can communicate a signal to a remote database. The signal can include a medicine dispensing history.

In another embodiment of the present invention, the one or more compartments can be configured to accept a medicine vial.

In some embodiments of this aspect, the apparatus can further include at least one sensor. The sensor can be configured to detect the presence or the absence of the medicine in the at least one compartment.

In another non-limiting aspect of the present invention, a system includes a housing. A door can be connected to the housing. The door can be commanded to an open position or a closed position to allow a user access to a medicine stored within the housing. A carousel can include a plurality of compartments. The carousel can be mounted to the housing, and can be commanded to rotate to at least one position associated with a location of the medicine. An interactive touchscreen can be connected to the housing. The touchscreen can be configured to command the door and the carousel to the at least one position associated with the location of the medicine. A processor can be connected to the housing. A cell network communicated with the processor for sending or receiving a telemetry data set to or from the cell network. A computer device can be connected with the cell network and can receive the telemetry data set for monitoring a compliance of a user with a predetermined schedule.

In some embodiments, the processor can be a machine to machine (M2M) cell radio processor.

In certain embodiments, the network can be a wireless cell radio network.

In several embodiments, the cell network can further include a machine to machine (M2M) secure virtual private network connection.

In certain embodiments of this aspect, the telemetry data set can include a name of a medicine, a strength of the medicine, and a time for dispensing the medicine.

In some embodiments of this aspect, the telemetry data set can include a time the door was opened, a time the door was closed, and a time the carousel was rotated to the at least one position associated with the location of the medicine.

In certain embodiments, the machine to machine (M2M) processor can send a signal to a remote database. The signal can include a dispensing history.

In some embodiments, the system can further include at least one sensor. The sensor can be configured to detect the presence or the absence of the medicine in the plurality of compartments.

In other embodiments, each of the plurality of compartments can be configured to accept a medicine vial.

In another aspect of the instant invention, a method can include the steps of entering a data set into a software application, wherein the software application can be executed on a main processor mounted to a housing; sounding an alarm at a predetermined medication time; commanding a carousel to move from a first position to a second position; commanding a door to move from a first position to a second position to allow a user access to items stored within the carousel; sending a data set from a cell radio processor to a cell network for use in patient compliance monitoring.

In one embodiment of this aspect, the cell network can be a M2M wireless private network.

DETAILED DESCRIPTION

As used herein, the terms medicine, pill and pills refer to any size or shape of a capsule, caplet, granule, tablet, lozenge, suppository, ampoule or any other dosage form typically used for oral nasal, dermal or rectal administration of a medication or dietary supplement or for rectal administration in the form of a suppository. The term pill or pills can include medications used for injections. The terms pill and pills may also include delivery forms typically used for topical administration, such as encapsulated and packaged liquid suspensions or emulsions, powders, creams, salves, serums, ointments and the like. The terms pill, medicine or medication may be singular or plural and are used interchangeably herein.

As used herein, the terms pill, medicine and or medication refer to prescription and over-the-counter medications, dietary supplements such as vitamins, minerals or cosmetic products. Further, the terms pill, medicine and or medication refer to any product in pill form which the user has a need or desire to use on a predetermined, scheduled basis. Further, the terms medicine and medicines can refer to any product which the user has a need or desire to use on a predetermined, scheduled basis.

As used herein, machine to machine (M2M) refers to direct communication between devices using any communications channel, including wired or wireless, cell or internet protocol (IP).

Machine to machine communication can include instrumentation, for example, that enables one or more sensors communicate the data recorded by the sensors to an application software that can use it. For example, to log a time that a medicine was dispensed and compare this time to an acceptable time range, or to record an alarm when no dispensing occurred within a specified compliance range. Such M2M communication can be accomplished by having a remote network of machines relay information back to a central hub for analysis, which can then be rerouted to a system such as a personal computer. Machine to machine communications can include a system of cell or IP networks that transmit data to and from personal medicine organizers to one or more monitoring systems or stations.

Some of the components of a non-limiting embodiment of the invention as described below may include the following elements: base 1, base tower 2, lid 3, door assembly 4, carousel assembly 5, retainer cover 6, LCD bezel 7, gear motor 8, pinion gear assembly 9, carousel position sensor processor board 10, vial sensor processor board 11, LCD touchscreen 12, light strip 13, door limit switch 14, antenna 15, battery strap 16, battery 17, speaker 18, main processor board 19, cell radio processor board 20, and power cable 21, housing 22, compartment 24, vial 26, door 28, IR sensor 30, interdigitating sensor tabs 32 and IR lens 34.

In one non-limiting embodiment of the present invention as shown in FIGS. 1-7, device 100 includes base 1, base tower 2, lid 3, and cover retainer 6 form an integral housing 22.

Door assembly 4 and door limit switch 14, to sense the position of door assembly 4, are attached to form an integral door assembly mechanism that can be closed or opened.

Carousel assembly 5 includes compartments 24 for storing and dispensing medicine vials 26 is mounting in the housing.

Gear motor 8 and pinion gear assembly 9 are configured to drive the position of the door and the carousel.

Carousel position sensor processor board 10, and vial sensor processor board 11, are configured to sense the position of the carousel, and the presence or absence or a vial in a compartment of the carousel respectively.

LCD touch screen 12, the primary user interface, is mounted to lid 3, using bezel 7.

This embodiment includes light strip 13 and speaker 18 which can be utilized to produce both visual or audio alarms to alert a user of, for example, a missed dose of medicine, or a time to dispense a medicine.

Cell radio processor board 20, and antenna 15 are configured to allow main processor board 19 to communicate wirelessly with a private cell network, such as an M2M network.

The unit 100, can be powered by battery 17, which is retained by strap 16 or through power cable 21 which can be connected to an AC power source.

The door assembly 4 can include a door 28 and is preferably transparent or translucent.

The unit 100 includes command capabilities to command the mechanisms to open or close and lock the door until a medication dose is scheduled to be taken and to rotate the carousel assembly to a predetermined position for dispensing one or more particular medicines at one or more particular times. The mechanism can be operated by using touchscreen 12. When a pre-determined time set in the main processor 19 occurs, an alarm can be trigger through speaker 18, or light strip 15 to alert the user. Further, the touch screen 12 will illuminate to alert the user and display a prompt for dispensing the proper medicine.

The housing 22 includes carousel assembly 5 for storing medicine vials 26. The carousel can include compartments 24, and one or more sensors 11, such as infrared sensor 30 configured to sense the presence or absence of a vial in a compartment. The sensor is protected by IR lens 34.

Interdigitating tabs on 32 on the carousel 5 pass through or between infrared sensors 30 on processor board 10. A particular pattern of tabs corresponds to a respective position of the carousel. The processor can read the on-off state of each sensor and decipher the combination of tabs 32 such that each position of the carousel is determined. This information is thereby translated to a particular compartment holding a known medicine.

The housing 22 also includes cell radio processor and associated hardware necessary to communicate telemetry data regarding the status of the device, including, for example, the time(s) the door is opened and closed, how many times the door was opened or closed, the position of the carousel, the dispensing history data. This information can be sent to a network hub or other device where it can be captured for analysis. Further, any authorized computer device can be connected to the network hub to obtain the telemetry data, giving authorized users the ability to analyze the telemetry data for use in monitoring a patient's compliance with a given medicine regimen.

In this embodiment, IR sensors 30 can be used to sense when a vial is in a compartment. Once a vial is removed from a compartment, the user will be prompted to take all of the medicines designated at according to a predetermined dosing schedule After dosing is completed, when the vials are replaced in the device, the door is closed and locked and the dosing program continues according to a preprogrammed schedule.

Next, the user can load medicine vials or other medicines into one or more compartments. Once loading is confirmed, the doors will close a programmed dosing regimen with commence.

In this embodiment, a scheduling application can be programmed to send the user an alarm, or a reminder, if the dosing time has passed, on the user's home phone or smart phone. The application can will illuminate the light(s) representing particular compartments corresponding with particular medicines on the touchscreen at pre-determined times.

When the user accesses the medicine, the processor 19 can electronically time stamp each time the door is opened or closed. This data can be sent to the network for review and analysis. After each use, the door is closed and locked. A timer in the application executed by the processor is used to determine when next dose is due, and the process is repeated.

The structure of the device can be fabricated from plastics or other structural materials and molding or fabrication processes which will be known to one skilled in the art of manufacturing.

The user interface has a graphical display designed for ease of use. The user is guided through a series of steps to set up and program the device, dispense medications and perform other desirable functions as described.

In use, a user or caregiver, such as a medical worker, can load one or more standard medicine vials into the compartments. The medicine labels will be conveniently visible to a user.

After loading, the door can lock the contents inside the housing. If the device is transported to a user's home, the device can be plugged in to an AC power source or otherwise powered by a battery, or in case of a power failure, the battery can a be a backup power source. Next, the dosing regimen can begin.

Once powered, the device connects wirelessly to an M2M private network to begin a preprogramed dosing schedule. For example, if three medicines are arranged in compartments or chambers 1, 2, and 3 respectively, the alarm will sound, or light at the preprogrammed dosing time, for example, 9 am. The alarm can be an audible alarm, and a visual alarm, such as the illuminated touch screen and light ring. The user is prompted to dispense the three medicines.

If the user forgets or does not respond the alarm, reminders can be sent to the user by phone or can alert a caregiver by phone or other electronic means such as a text message or email. Further, the telemetry is sent and recorded at the hub, which can be accessed such as by a computer in a hospital for example, thereby allowing recording and monitoring of compliance and non-compliance.

In some embodiments, the application can be programmed to send the user an alarm, such as a reminder phone call on a smart phone or home phone and illuminate the light(s) in the appropriate compartments at pre-determined times.

In some embodiments, the locking mechanism can include an independent locking system for each compartment and corresponding lid such that a vial placed in a compartment by a user can be electronically locked or unlocked in the compartment according to a dosing schedule. Preferably a corresponding illumination and de-illumination of the associated light alerts a user to see which compartment or vial is unlocked to access the proper medicine at the appropriate time Alternately, a central locking mechanism can be use such that a lock controller can rotate within the housing to the appropriate position in order to unlock the compartment and lid containing the medicine vial(s) at the predetermined times(s).

It is envisioned that the control system can be programmed to allow only one compartment to be open at a given time. This feature is designed for safety. That is, one compartment at a time is closed or open. The user takes the medicine, returns the vial and the carousel rotates after the user enters a command through the touch screen. The light is extinguished and the compartment is rotated. The process is repeated with the next medicine of interest. In this way, the user must replace the vial in the proper compartment thereby preventing unauthorized use or misuse of the correct medicine and ensuring compliance with the pre-programmed dosing schedule for one or more medicines.

It will be understood by a person of ordinary skill in the mechanical arts that the components for a locking mechanism of either configuration can be constructed from known materials using standard manufacturing methods.

Example

In use, a doctor can explain to a patient that medication will be necessary to effectively treat the patient's condition.

A medication schedule, specifying dose and frequency can be provided to the patient. Once the schedule is determined, the clinical nurse educator or the patient's pharmacist, or the patient can program an application that resides on medicine dispenser with the details of the patient's medication schedule.

For example, the patient may be required to take three pills three times each week, on Monday, Wednesday and Friday, mornings at 10:00 am.

In practice, on Monday, Wednesday and Friday morning at 10:00 am each week the organizer will sound an alarm reminding the patient that one or more medicines are scheduled.

If the appropriate compartment where the scheduled medicine is stored is not opened within a preselected time window, a sensor sends a signal via the M2M network, which in turn can send a reminder or message, for example, a phone call, e-mail or a text message, to the patient, the patient's caretaker or a health care professional.

After the device is programmed and loaded, the device will alert the user when it is time to take the appropriate medication. First, the device signals the user with a visual or audible alarm or both. At the same time, the LCD screen can display a visual alert.

Self-Loading or Reloading.

In operation, a user is presented with a touch screen interface. As shown in FIG. X, a welcome message indicates that a schedule has been set up and asks the user if they would like to load medications. A "start loading" icon button is presented. The display includes highlight for the carousel positions that correspond with each of the medications to be loaded and dispensed. A central "help" button causes a help menu to appear as will be discussed below.

The user presses the "start load" button causing the carousel to rotate to the desired positon, open the door and prompt the user to load the medicine into the desired location. For example, "load medication #1". The user may refer to a printed medication guide which identifies which medicine should go in which compartment. The device will continue to prompt the user repeating the above steps until all medicines are loaded in proper compartments. Designated areas on the touch screen will now show that the loading is complete by, for example, changing from a highlighted outline color when ready for loading, to a solid color when loading is complete.

After loading is complete the home screen will be displayed. The home screen display includes, the current time, today's schedule, and "more". Today's schedule will display the time for each dose, the next dose time will be presented in larger font for easy reference.

Once a dose time event has passed, a check mark will appear next to the time, thus indicating that the dose has been dispensed. A "X" will appear next to a dose time that has not been dispensed. The next dose time will again be highlighted in larger font.

When it is time to take a dose, the home screen will automatically transition to a dispensing screen. The screen will include a message such as "it is 10:00 am, dose is ready, please press the button to dispense". After the user presses the button, the screen shows the user which location(s) are to be dispensed. The carousel, controlled by logic in the processor and gear mechanisms, rotates to the correct location, and the door opens allowing access to the medicine. The user is now instructed to take each medicine according to the label instructions and replace each vial in the compartment. The process is repeated until all medicines for a given time are dispensed. After completion, the display returns to the home screen, which now shows completion status of the dose just dispensed. The next dose time is now highlighted to emphasize and remind the user of the time of the next dose.

As discussed above, the user will be presented with "more" button on the home screen. When depressed, the user is presented with five choices. Help, Dispense Medication, Load Medication, Review Prescription Label, and "go back" to return to the home screen.

Although not recommended, the user has the flexibility to override the schedule by pressing Dispense Medication. A screen will appear asking which compartment is to be dispensed, and a warning will be displayed to tell the user it is not time to take this medication and asking for further confirmation of the action. Once confirmed by the user pressing Yes, and the user will be allowed to dispense the medication as discussed above.

If more medication loading is required, the user presses Load Medication. The user will be prompted to select a location. The carousel will rotate and the door will open thus exposing the desired compartment. The user can now replace an empty or near empty vial with a refill of the appropriate medicine.

When it is necessary to review one or more labels at a time outside of a scheduled dose, the user can press Review Prescription Label. The user will be prompted to select a location. The carousel will rotate and the door will open thus exposing the desired compartment. The user can now inspect the label and return the vial to the compartment.

In this case the telemetry sent via M2M communications network to the hub will differentiate that this was not a dosing event. All other dosing events (e.g. time, location) will be recorded and the data communicated for compliance monitoring.

A patient database can be maintained on t a secure server. The database can be synchronized regularly with each device connected to the network. The network can be a cell phone network, a Wi-Fi network, or any other type of wireless or wired network.

Dispensing data can be communicated to a remote server database; the data is then available for review by the user or a care giver. The data may be presented in any number of ways including charts, graphs or tables. In this way, the user's medication dispensing history can be reviewed for compliance with the desired schedule for taking any medications.

In one embodiment, the application includes a feature which alerts a care taker that a dose has not been dispensed via a wireless network. For example, application generates a phone message, text message or e-mail message which is sent directly to the user, care taker, doctor or any number of interested parties. This feature can be particularly useful when, for example, a care taker or family member desires to monitor the medication dispensing compliance of a senior citizen such as a parent or family member or individual who may be suffering from a memory disorder or who may simply be forgetful. When the user receives a "missed dose" message, appropriate action can be taken in real-time to correct the short-term non-compliance and address the longer-term issues associated with the inability or unwillingness of a patient to comply with a medication schedule.

The device 100 includes a software application and central processor configured to store a medicine and schedule data for one or more medications. The processor stores medicine and schedule information that is input by a user. When a dose is dispensed, or missed by the user, the network processor can communicate with a secure server database. The server database can be accessed by users having a password and a username. Authorized users can login to the database to monitor patient compliance.

It is contemplated that numerous graphs and reports can be displayed or printed such that the person accessing the database can easily recognize compliance problems, determine whether there are any recurring compliance problems, or print medication lists.

The present invention allows a nurse, doctor, EMT or other health care professional to access a patient's medication regimen or dispensing history by accessing a secure database. This feature can dramatically reduce the risk of prescribing the wrong medication and also reduce the time before necessary treatment is administered.

Figure 1:
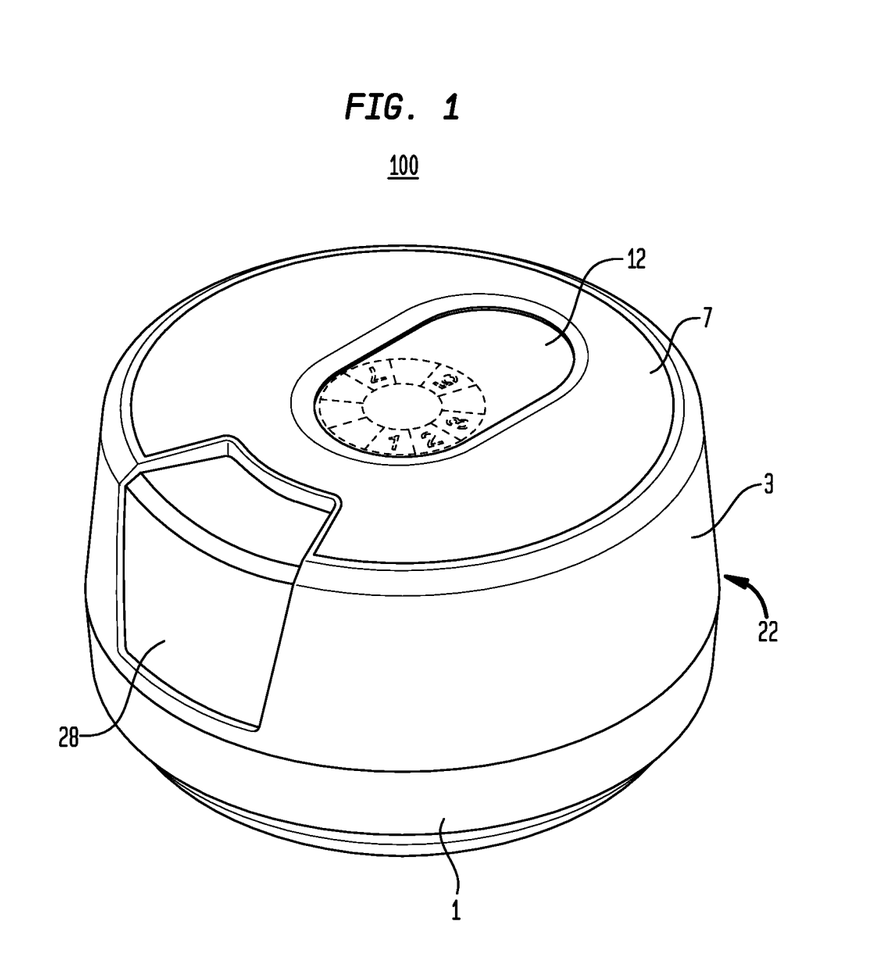
FIG. 1 is an isometric view of an interactive medication management device according to one embodiment of the present invention in a closed position.
Figure 2:
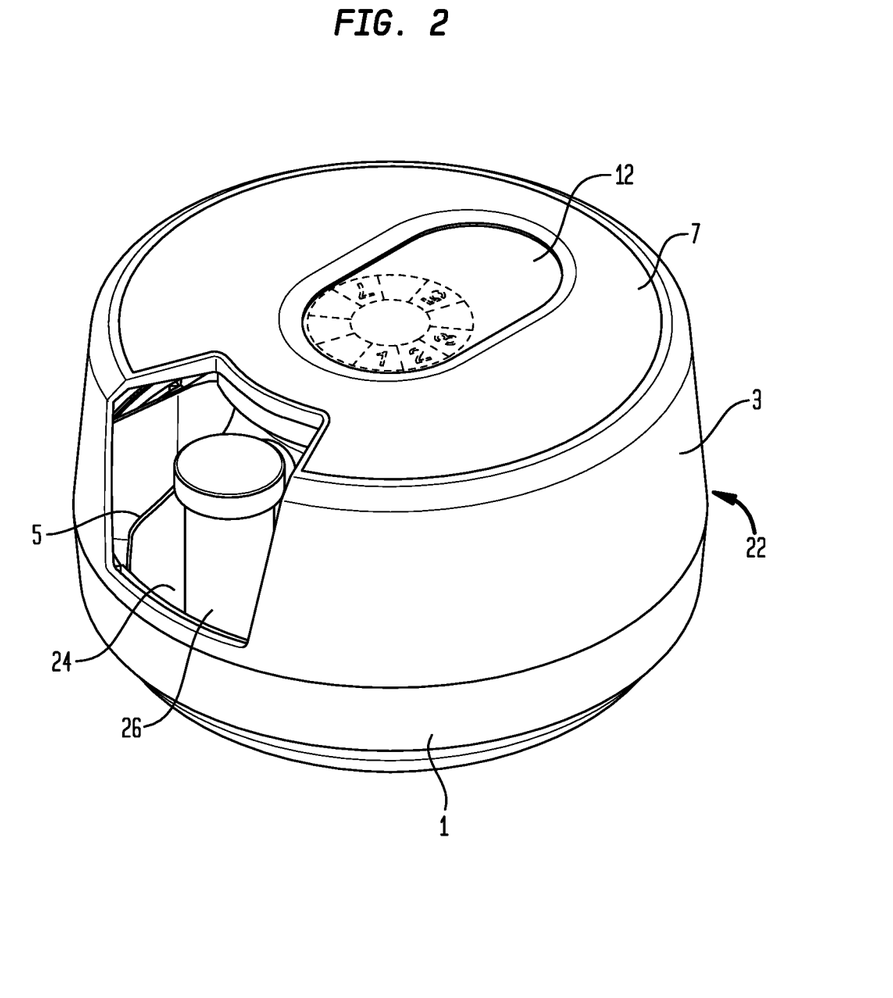
FIG. 2 is an isometric view of an interactive medication management device according to one embodiment of the present invention in an open position showing a stored medicine vial.
Figure 3:
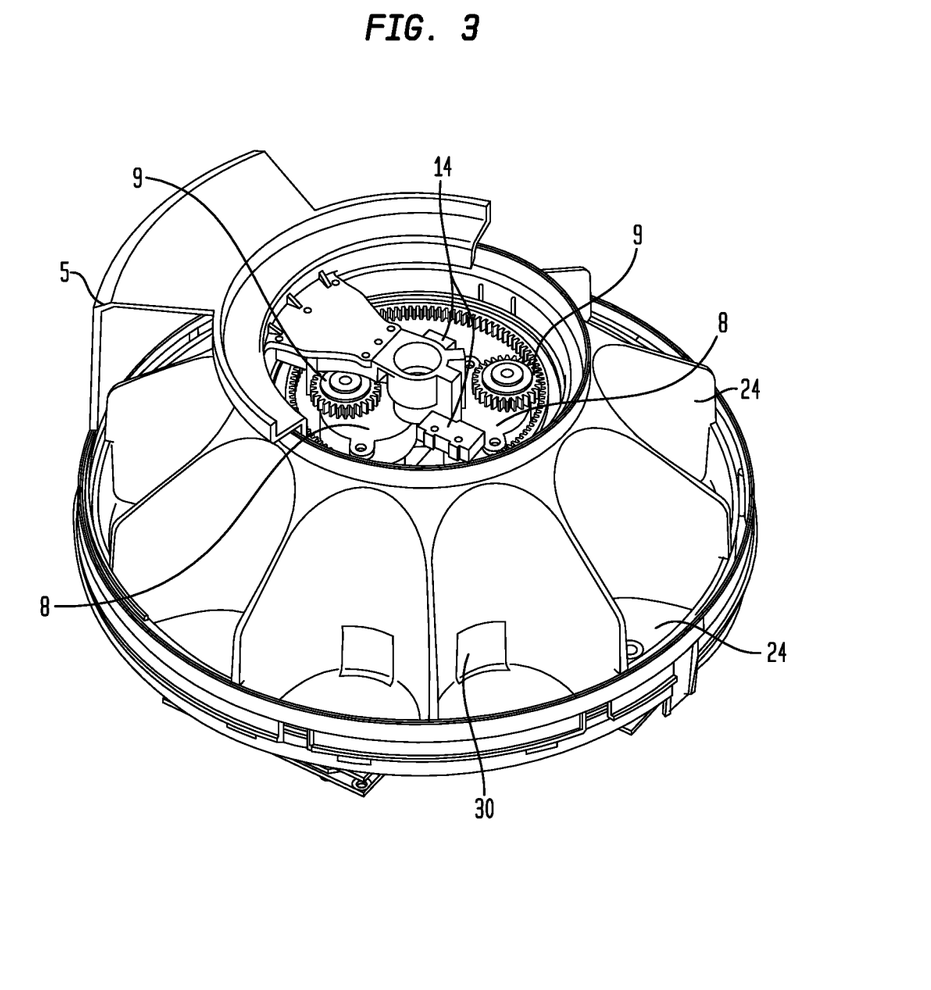
FIG. 3 is an isometric view depicting some of the elements included in the interactive medication management device of FIG. 1.
Figure 4:
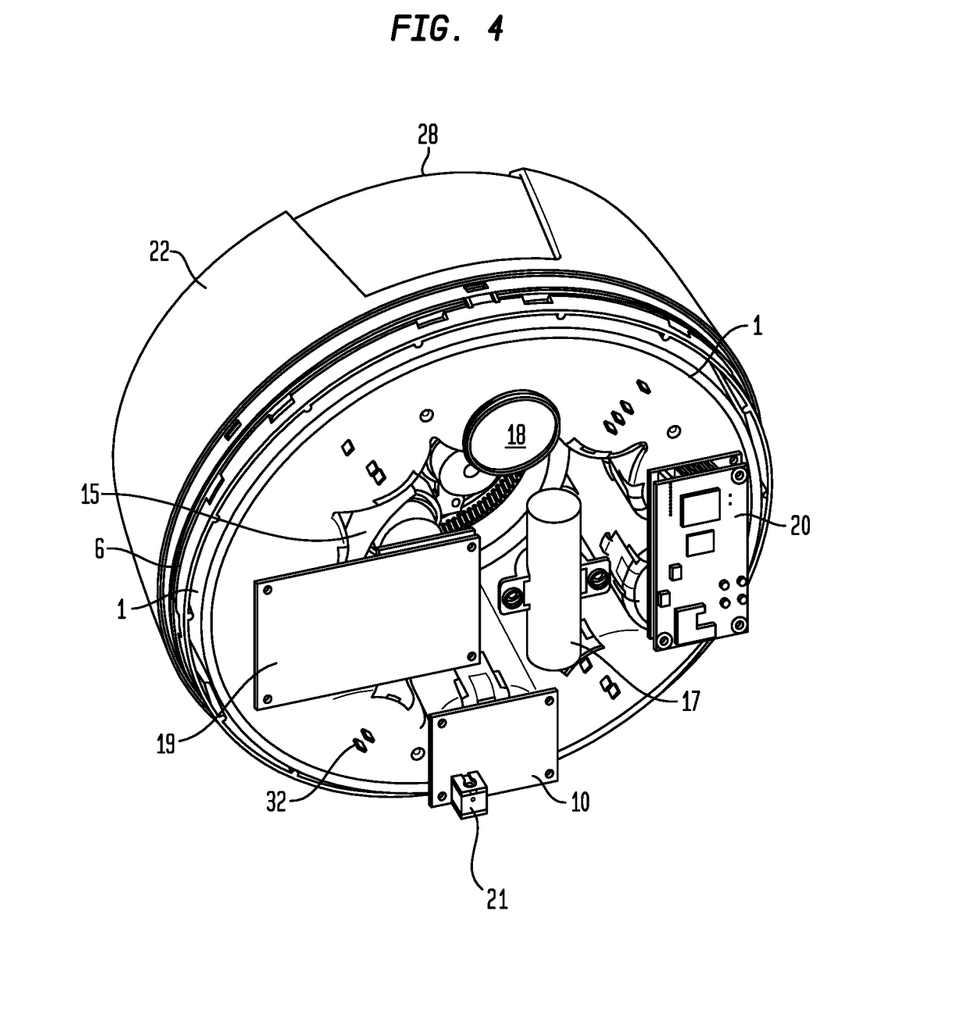
FIG. 4 is a bottom side isometric view depicting some of the elements included in the interactive medication management device of FIG. 1.
Figure 5:
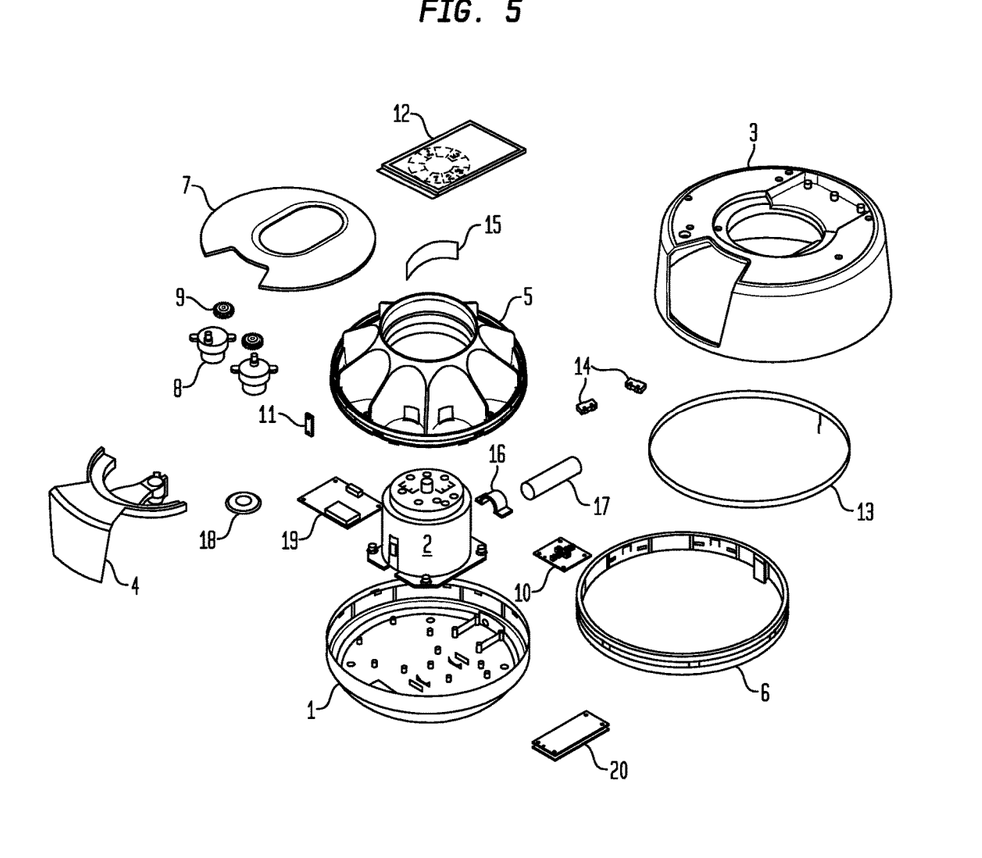
FIG. 5 is an exploded view depicting of some of the elements included in the interactive medication management device of FIG. 1.
Figure 6:
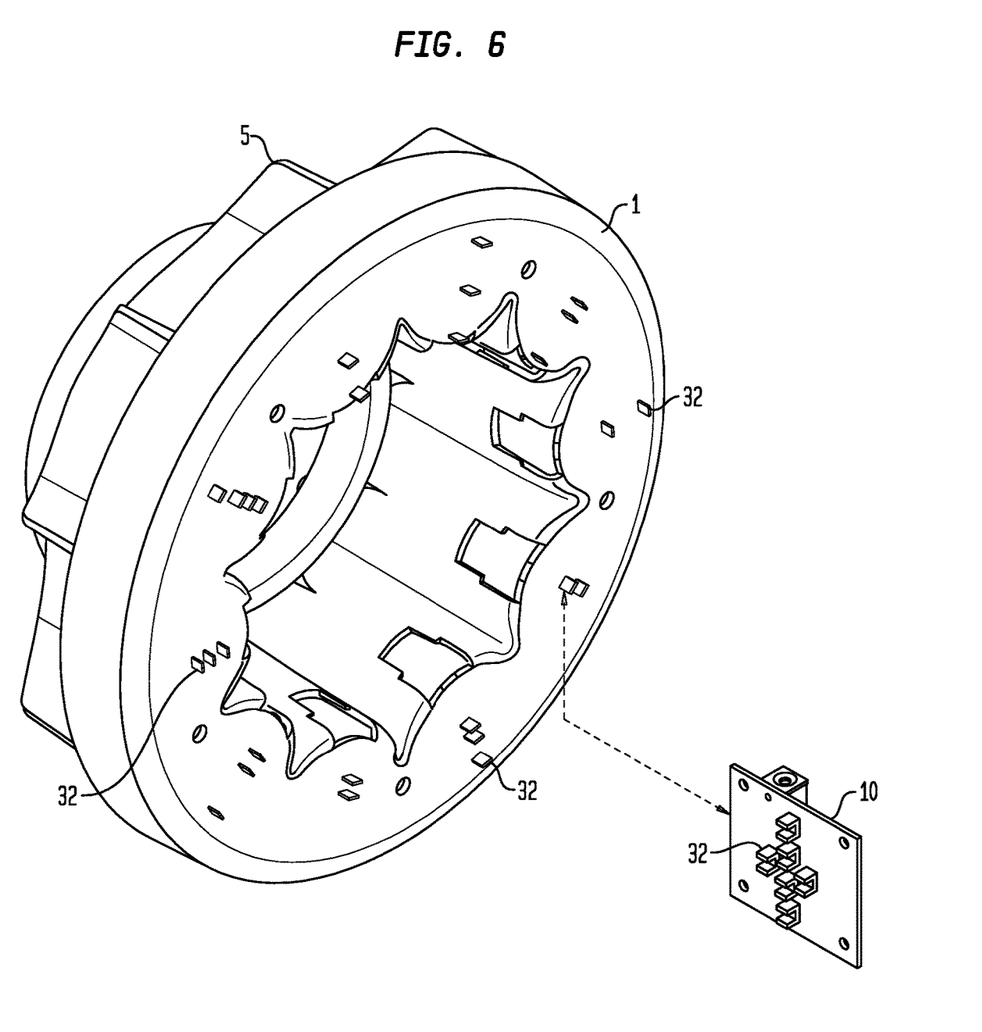
FIG. 6 is an isometric view depicting of some of the elements included in the interactive medication management device of FIG. 1.
Figure 7:
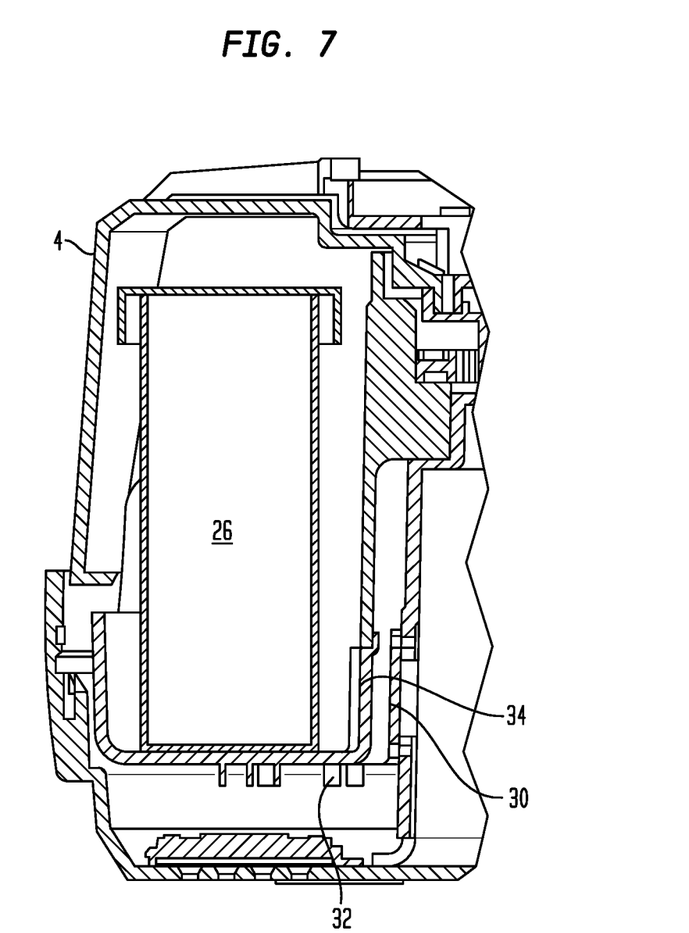
FIG. 7 is a cross-sectional view of some of the elements included in the interactive medication management device of FIG. 1.
Figure 8:
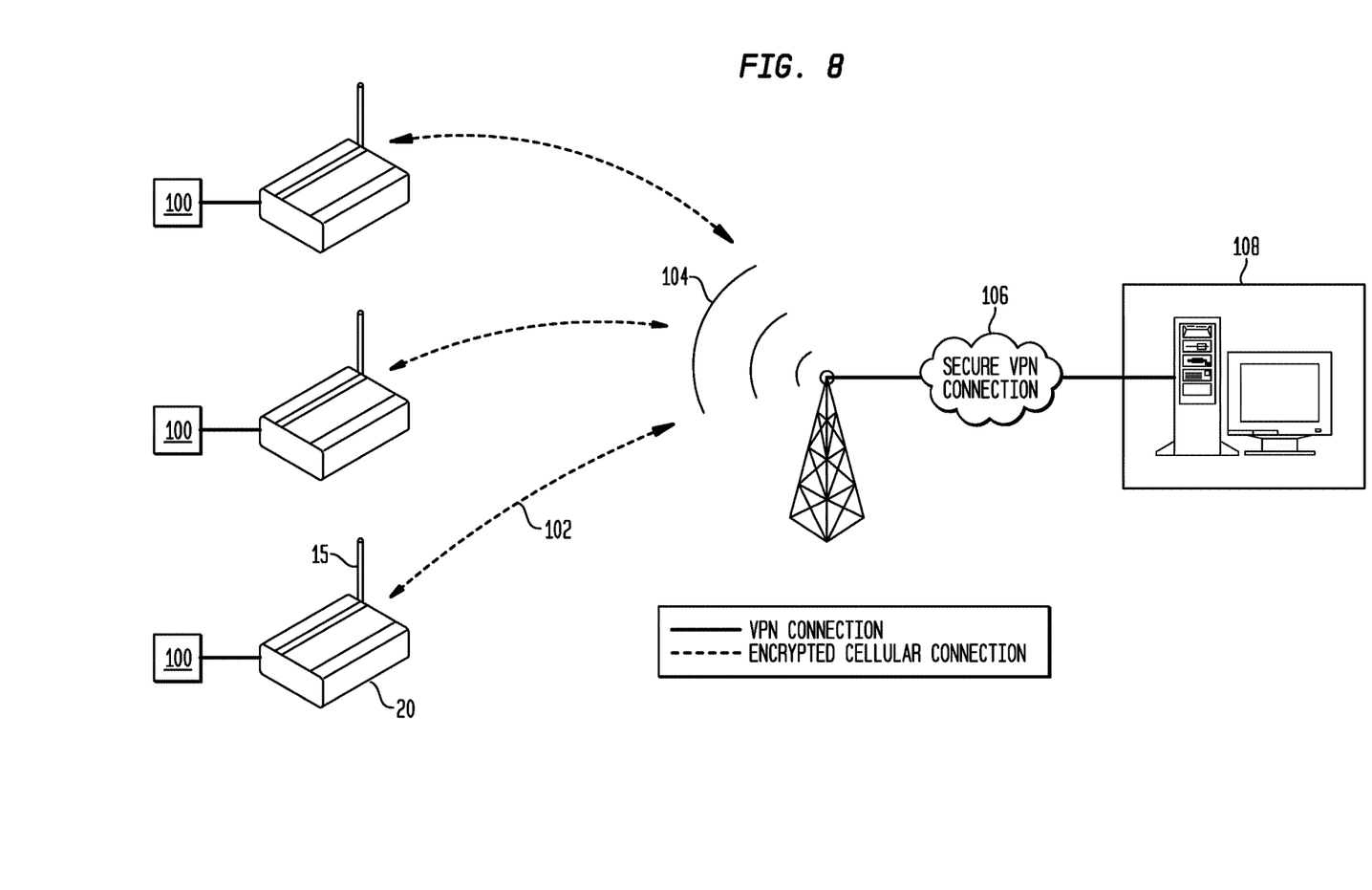
FIG. 8 is flow chart depicting some of the elements included in an interactive medication management system of the instant invention.

Referring to the system of FIG. 8, devices 100, each including a cell processor 20 and an antenna 15, can communicate using an encrypted cellular connection 102 with a cellular network 104. The network includes a secure virtual private network (VPN) connection 106. In this embodiment, a remote data station 108 including a computer processor can connect to the VPN for monitoring patient compliance with a medicine schedule. In this way, telemetry data, for example, such as dispensing time, carousel position, dispensing history, success or failure to dispense at within a given time window, can be captured by the data station and utilized to take corrective actions to reduce or eliminate non-compliance for a plurality of different patients and a plurality variable medication schedules.

Although the invention herein has been described with reference to particular embodiments, it is to be understood that these embodiments are merely illustrative embodiments and that other arrangements may be devised without departing from the spirit and scope of the present invention as defined by the disclosure herein.

What is claimed is:

1. An apparatus comprising:
   (a) a dispenser body having a housing;
   (b) a door, said door being connected to said housing, said door being commandable to an open position or a closed position to allow a user to load or to access a medicine stored within said housing;
   (c) a carousel, said carousel having at least one compartment, said carousel being mounted within said housing, said carousel being commandable to rotate said at least one compartment to at least one position associated with a location of said medicine;
   (d) an interactive touchscreen, said touchscreen being mounted within said housing, said touchscreen being configured to command said door to an open or a closed position and to command said carousel to said at least one position associated with a location of said medicine;
   (e) an antenna, said antenna being mounted within said housing;
   (f) a sensor assembly, said sensor assembly being configured to detect the presence or the absence of said medicine in said at least one compartment, said sensor assembly including a plurality interdigitating tabs configured to provide location data for a plurality of carousel positions, said plurality of interdigitating tabs protruding from said carousel, wherein an infrared sensor provides an on-off state to decipher a particular combination of said plurality of interdigitating tabs corresponding to said at least one compartment holding a known medicine; and
   (g) a machine to machine (M2M) cell radio processor, said processer being mounted within said dispenser body housing, said processor being capable of communicating with a wireless cell radio network, wherein said processor sends or receives a telemetry data set to said network for monitoring a compliance of a user with a predetermined medicine schedule, said network further including a machine to machine (M2M) secure virtual private network connection.

2. The apparatus of claim 1, wherein said telemetry data set comprises: (a) a name of a medicine, (b) a strength of said medicine, and (c) a time for dispensing said medicine.

3. The apparatus of claim 1, wherein said telemetry data set comprises: (a) a time said door was opened, (b) a time said door was closed, and (c) a time said carousel was rotated to the at least one position associated with a location of said medicine.

4. The apparatus of claim 1, wherein said machine to machine (M2M) processor communicates a signal to a remote database, said signal indicating a medicine dispensing history.

5. The apparatus of claim 1, wherein said at least one compartment is configured to accept a medicine vial.

6. A system comprising:
   (a) a dispenser body having a housing;
   (b) a door, said door being connected to said housing, said door being commandable to an open position or a closed position to allow a user access to a medicine stored within said housing;

(c) a carousel, said carousel having a plurality of compartments, said carousel being mounted within said housing, said carousel being commandable to rotate to at least one position associated with a location of said medicine, said carousel including a plurality of interdigitating tabs protruding from said carousel, wherein an infrared sensor provides an on-off state to decipher a combination of said plurality of interdigitating tabs corresponding to a particular compartment storing a known medicine;

(d) an interactive touchscreen, said touchscreen being mounted within said housing, said touchscreen being configured to command said door and said carousel to said at least one position associated with said location of said medicine;

(e) a processor, said processer being mounted within said housing;

(f) an antenna, said antenna being mounted within said housing;

(g) a cell network, said network being capable of communicating with said processor for sending or receiving a telemetry data set to or from said cell network, wherein said data set includes (a) a name of a medicine, (b) a strength of said medicine, and (c) a time for dispensing said medicine (d) a time said door was opened, (e) a time said door was closed, and (f) a time said carousel was rotated to at least one position associated with a location of said medicine; and (h) a computer device, said device being capable of connecting with said cell network and being capable of receiving said telemetry data set for monitoring a compliance of a user with a predetermined schedule.

7. The system of claim 6, wherein said processor is a machine to machine (M2M) cell radio processor.

8. The system of claim 6, wherein said cell network further includes a machine to machine (M2M) secure virtual private network connection.

9. The system of claim 8, wherein said network is a wireless cell radio network.

10. The system of claim 6, wherein said machine to machine (M2M) processor sends a signal to a remote database, said signal including a dispensing history.

11. The system of claim 6, further including a sensor assembly, said sensor assembly being configured to detect the presence or the absence of said medicine in said plurality of compartments, said sensor assembly including a plurality interdigitating tabs configured to provide location data for a plurality of carousel positions.

12. The system of claim 6, wherein each of said plurality of compartments is configured to accept a medicine vial.

13. A method comprising:
(a) entering a first data set into a software application, said first data set including a name of a medicine, (b) a strength of said medicine, and (c) a time for dispensing said medicine, said software application being executed on a main processor mounted within a housing;

(b) sounding an alarm at a predetermined medication time;

(c) commanding a carousel to move from a first position to a second position, said carousel being mounted within said housing;

(d) commanding a door to move from a first position to a second position to allow a user access to items stored within said carousel, said carousel including a plurality interdigitating tabs configured to provide location data for a plurality of carousel positions, said plurality of interdigitating tabs protruding from said carousel, wherein an infrared sensor provides an on-off state to decipher a particular combination of said plurality of interdigitating tabs corresponding to a compartment holding a known medicine; and (e) sending a second data set from a cell radio processor to a M2M wireless private cell network for use in patient compliance monitoring, said second data set including, a time said door was opened, a time said door was closed, and a time said carousel was rotated to at least one position associated with a location of said medicine, wherein said cell radio processer is mounted within said housing.

* * * * *